US009983102B2

(12) United States Patent
Staymates et al.

(10) Patent No.: US 9,983,102 B2
(45) Date of Patent: May 29, 2018

(54) AERODYNAMIC SHOE SAMPLING SYSTEM

(75) Inventors: Matthew Staymates, Germantown, MD (US); Stefan Robert Lukow, Galloway, NJ (US)

(73) Assignee: The United States of America, as represented by the Secretary of Homeland Security, Washington, DC (US)

( * ) Notice: Subject to any disclaimer, the term of this patent is extended or adjusted under 35 U.S.C. 154(b) by 1040 days.

(21) Appl. No.: 13/440,857

(22) Filed: Apr. 5, 2012

(65) Prior Publication Data

US 2012/0255376 A1 Oct. 11, 2012

Related U.S. Application Data

(60) Provisional application No. 61/472,940, filed on Apr. 7, 2011.

(51) Int. Cl.
*G01N 1/02* (2006.01)
*G01N 1/22* (2006.01)

(52) U.S. Cl.
CPC ......... *G01N 1/22* (2013.01); *G01N 2001/022* (2013.01); *G01N 2001/024* (2013.01); *G01N 2001/2223* (2013.01)

(58) Field of Classification Search
CPC ............. G01N 1/22; G01N 2001/2223; G01N 2001/022–2001/027
See application file for complete search history.

(56) References Cited

U.S. PATENT DOCUMENTS

| | | | |
|---|---|---|---|
| 4,045,997 A | 9/1977 | Showalter et al. | |
| 4,202,200 A | 5/1980 | Ellson | |
| 4,896,547 A | 1/1990 | Arney et al. | |
| 4,909,089 A * | 3/1990 | Achter et al. | 73/863.11 |
| 4,987,767 A | 1/1991 | Corrigan et al. | |
| 5,109,691 A | 5/1992 | Corrigan et al. | |
| 5,585,575 A | 12/1996 | Corrigan et al. | |
| 5,741,984 A * | 4/1998 | Danylewych-May et al. | 73/864.71 |
| 5,753,832 A | 5/1998 | Bromberg et al. | |
| 5,760,314 A | 6/1998 | Bromberg et al. | |
| 5,915,268 A | 6/1999 | Link et al. | |
| 6,073,499 A | 6/2000 | Settles | |
| 6,334,365 B1 * | 1/2002 | Linker et al. | 73/864.81 |
| 6,375,697 B2 | 5/2002 | Davies | |
| 7,047,829 B2 | 5/2006 | Napoli | |
| 7,357,044 B2 | 4/2008 | Sleeman et al. | |
| 7,543,478 B2 * | 6/2009 | Burroughs et al. | 73/28.01 |
| 7,636,036 B2 * | 12/2009 | Manneschi | 340/454 |

(Continued)

*Primary Examiner* — Robert R Raevis
(74) *Attorney, Agent, or Firm* — Lavanya Ratnam; Trenton Roche; William Washington

(57) ABSTRACT

The apparatus disclosed herein pertains to the detection of trace explosives or narcotics detection. The apparatus comprises the front-end particle dislodge and sample intake portion of a chemical trace detection system utilizing aerodynamic flow as a transport mechanism whereby compounds indicative of explosives or narcotics contamination are liberated from target surfaces of foot or footwear and then transported by air flow to a sample accumulation feature for chemical analysis. The apparatus is intended for inclusion with additional components, such as an efficient pre-concentrator, a thermal desorption unit, and a chemical analyzer/detector to achieve a complete trace detection system.

1 Claim, 2 Drawing Sheets

(56) References Cited

U.S. PATENT DOCUMENTS

| | | | | |
|---|---|---|---|---|
| 8,429,987 | B1 * | 4/2013 | Linker et al. | 73/864.33 |
| 2006/0081073 | A1 * | 4/2006 | Vandrish et al. | 73/864.33 |
| 2007/0056396 | A1 * | 3/2007 | Mawer | 73/866 |
| 2008/0053252 | A1 * | 3/2008 | Jenkins et al. | 73/864.33 |
| 2009/0044641 | A1 * | 2/2009 | Konduri et al. | 73/863.11 |

* cited by examiner

AERODYNAMIC SHOE SAMPLING SYSTEM

RELATED APPLICATIONS

This application claims priority under 35 U.S.C. § 119(e) to U.S. Provisional Application Ser. No. 61/472,940, entitled "Aerodynamic Shoe Sampling System," filed on Apr. 7, 2011.

BACKGROUND OF THE INVENTION

The invention disclosed herein relates to the non-intrusive inspection of unadorned feet or footwear (hereafter referred to as footwear) for trace explosives or narcotics detection, more particularly an intake apparatus utilizing accelerated airflow to dislodge and collect trace chemical compounds from footwear. The invention is of particular application at inspection for entry of government and military installations and during inspection procedures of persons attempting to board commercial aircraft.

Systems used to detect the presence of trace amounts of chemicals indicative of explosives or narcotics presently exist and are of significant value to customs and law enforcement officials worldwide. These systems utilize a variety of methods to collect and analyze chemicals of interest. Generally the chemicals of interest to be detected by these systems are present in minute or trace quantities on the surface of a subject or object and consequently any method of chemical detection utilized must be extremely sensitive and prevent loss of sample during collection for analysis. Devices that utilize aerodynamic sampling to remove trace particulate matter from target surfaces exist in the prior art but do not ensure that all dislodged particles are transported efficiently to a collector. Such devices are ineffective at maximizing the transport efficiency of particles once they are liberated from surfaces due to loss or spillage out of the domain of the sampling system where such particles escape detection. The invention minimizes spillage or washout of the sample during collection from the targeted surface.

SUMMARY OF THE INVENTION

Terrorists and other criminals who come into contact with certain contraband are likely to become contaminated by trace deposits of those contraband materials through active or passive transfer of compounds of interest. Identification of these chemical compounds of interest and the individual that has likely come into contact with the contraband will allow authorities to screen for terrorist and narcotics traffickers more effectively. The invention is directed toward the utilization of aerodynamic sampling means incorporating high-pressure air jets and air knives effectively to remove small particles of explosives, narcotics and other chemical agents from target footwear surfaces. The liberation of these chemical agents of interest from targeted surfaces through aerodynamic means by the invention eliminates the occurrence of sample loss through sampling methods incorporating a physical method of sample abstraction such as brushes or wipe cloths.

The present invention liberates trace chemical compounds from the surface of targeted footwear; then transport the liberated matter to an area of sample accumulation through a contoured channel while liberated matter is simultaneously held aloft within a high-velocity bulk air flow field established by the geometry of the channel and a primary air mover. Subsequent to collection at a sample accumulation feature such liberated matter may be subject to analysis or detection of chemical composition.

DESCRIPTION OF THE INVENTION

Aerodynamic sampling of people, cargo, and other objects is an emerging technology for high-throughput, non-contact trace explosives screening at security checkpoints. Non-contact sampling provides an objective analysis without the need for physical contact, and offers high-throughput which can reduce backups and long lines. The technology can be based on fundamental principles from fluid mechanics, gas dynamics, and thermodynamics and when implemented properly, and can be used to efficiently transport an explosive sample from a surface to a collector. The invention described herein relates to the "front end" sample extraction portion of a chemical analysis system. The invention liberates particulate matter from footwear substrate and ensures that all the released material is transported by aerodynamic means to a location for subsequent collection and analysis.

Of particular concern to law enforcement authorities is the concealment of explosives in shoes; this type of concealment has lead to the requirement for all airline passengers to have their footwear removed and screened. Sampling footwear without removing them could potentially lead to significant improvements in screening throughput time and passenger compliance. This invention comprises devices for removing and transporting trace chemical residues from footwear surfaces to an accumulation feature without the use of intrusive physical contact as exhibited by devices utilizing brushes or swabs. The device is based on the aerodynamic characterization of airflow from various gas delivery vehicles, primarily pressurized gas released from air jets and air knives impinging off footwear surfaces and the consequent removal and transport of trace particles released from the footwear surface by that airflow. The invention liberates chemical compounds from a targeted surface, even if the trace compounds are embedded in sticky sebaceous material through the aerodynamic shear forces applied to a targeted area by an air jet or air knife.

The invention uses aerodynamic means to liberate matter from footwear, such means comprising one or more mounts of variable length, which are affixed to one or more high-pressure gas delivery vehicles that direct high-velocity air flow directly at the outer and inner portions of footwear and above any tongue of the footwear (such mounts are used to affix said high pressure gas delivery vehicle to a channel leading to a sample accumulation feature). The gas delivery vehicles of the invention comprise air jets or air knives. Each gas delivery vehicle is attached to a source of compressed gas, atmospheric or otherwise. In its best embodiment the gas delivery vehicles should be positioned for the released airflow to impact a substantial portion of the target surface and near enough to allow the airflow to assert sufficient pressure to dislodge particles from the target surface. The high aerodynamic shear force delivered by the pressurized gas onto the surface of the target footwear liberates particulate matter from targeted areas.

An air moving device is used to draw atmosphere into a contoured channel. Target footwear surfaces are positioned outside or partially outside of the channel inlet. Allowable distance of targeted footwear from the opening of the intake channel will vary in direct relation to airflow and gas delivery vehicle positioning. Such distance of footwear from channel should be optimized in relation to the total rate of airflow entering the channel and dimension of channel mouth in order to reduce spillage of sample from the channel mouth during sample intake. The contoured channel is connected to a sample accumulation feature whereby the sample compounds accumulate into a concentrated state before desorption or chemical analysis. A primary air moving means comprising a blower, vacuum pump or other device for drawing atmospheric air is connected to the channel feature for drawing atmospheric air through the channel, to and through, the location where a sample accumulation feature captures particulate matter for analysis. During sample procurement, the primary air moving means should draw atmosphere through the mouth of the channel at a steady-state operating flow rate above 400 liters of atmospheric air per second (lps) at ambient temperature. For subjects of atypical size or stance, height and width dimensional measurements for the channel mouth may require reconfiguration. If reconfiguration is required, a refinement of the steady state operating flow rate will be required if the change in configuration of the channel mouth causes a decrease in flow rate. Sample procurement will occur while targeted footwear is positioned within a stream of airflow operating at steady state. To ensure procurement of sample, the gas delivery vehicles positioned around the target footwear expel pressurized gas in a predetermined sequence designed to efficiently liberate contraband particles from the footwear surface. Once liberated from the footwear surface, the atmosphere being drawn into the channel by the primary air mover will transport the liberated particles through the channel to the sample accumulation feature.

In its best embodiment, the invention required an in-depth study of jet timing and sequencing parameters to determine the optimal configuration to minimize spillage. Firing a plurality of gas delivery vehicles at the same time caused the steady state airflow produced by the primary air mover to destabilize and result in significant spillage of liberated particles from the channel domain. Several timing sequences for the gas delivery vehicles were developed and studied using flow visualization to determine their influence on the overall flow field. The firing configuration for the gas delivery vehicles to ensure consistent particle release and transport in this invention is limited by the required sampling time for a specific implementation and will be dependent upon the sample processing speed of the chemical detection device and amount of airflow introduced into the system by the gas delivery vehicles. To a certain degree, the more times the gas delivery vehicles impact the target footwear with high pressure gas, the more particles will be removed. However, practical limitations in a field deployed environment would likely limit the overall sampling time to several seconds. A firing solution comprising delivery of a pressurized gas stream to the inside of footwear, outside of footwear and over tongue of footwear should be determined and repeated a plurality of times. The total number of pressurized gas releases by the gas delivery vehicles will be dependent upon sampling time allotted in accordance with field conditions.

BRIEF DESCRIPTION OF THE DRAWINGS

The features of the invention embodiment are described, with reference to accompanying drawings.

DETAILED DESCRIPTION OF THE PREFERRED EMBODIMENT DRAWINGS

Figure 1:
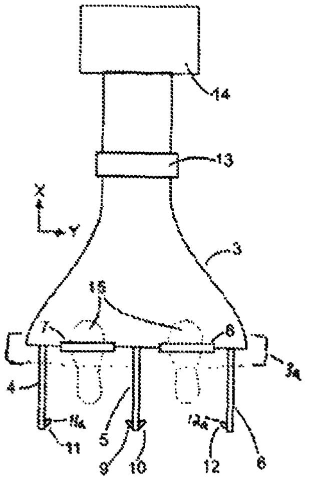
FIG. 1 illustrates the invention from above with orientation in the X-Y plane.

Referring first to FIG. 1, which has a view that is oriented in the X-Y plane, the apparatus of the present invention includes a main sampling structure comprised of a converging channel 3 for intake of sample containing air, four EXAIR super air nozzle (Model no. 1100)-air jets 9, 10, 11, 12, three air jet mounts 4, 5, 6 extending outward from the intake portion of the channel 3*a*, two EXAIR super air knife (Model no. 110003) 7, 8 and a Chicago Blower Corp. (serial no. 254919-2, part no. 7042535) 2-horsepower centrifugal blower as a primary air moving unit 14. The air sample intake channel 3 is contoured in a converging shape to prevent air recirculation patterns from forming within corners. The central air jet mount 5 has a left central air jet nozzle 9 and a right central air jet nozzle 10 attached at the portion of the mount opposite the intake portion of the channel 3*a*. The left air jet mount 4 has one air jet nozzle 11 attached at the portion of the mount opposite the intake portion of the channel 3*a* and the right air jet mount 6 has one air jet nozzle 12 attached to the mount at the portion of the mount opposite the intake portion of the channel 3*a*. The converging channel 3 contains a sample accumulation feature 13. The collection device 13 is the portion of the invention where sample is collected for testing, this portion may take the form of a pre-concentrator or any means utilized to isolate the sample for analysis. The sample accumulation feature 13 is incorporated within the channel 3 but may in an alternative embodiment be linked to the channel 3 through a bypass mechanism which does not allow air to continuously flow through the sample accumulation feature 13 while the primary air mover 14 is in operation. Air is drawn through the collection device by a primary air mover 14 operating at an ideal flow rate of above 600 liters per second. The flow rate of the primary air mover 14 is an essential element of this invention. Laser light sheet flow visualization experiments using theatrical fog and talc powder have demonstrated that spillage is minimized when the air mover 14 is operating at the optimal flow rate of 620 liters per second through a rectangular channel intake area with a dimensional range from 30-40 inches in width to 4-8 inches in height. Optimal dimensions for such rectangular channel intake area are 34 inches wide by 6.5 inches high 3*a*. If the flow rate is too low, excess air introduced by the jets 9, 10, 11, 12, and air knives 7*a*, 8*a* can overload the system and spill sample laden air from the intake portion of the channel 3*a*. This will reduce the effectiveness of sampling and particle collection. At a flow rate of 620 liters per second, all particles that are liberated from the footwear surfaces are transported directly through the intake portion of the channel 3*a*. Outlines of footwear patterns 15 are located beneath the left air knife 7*a* and right air knife 8*b* to indicate the location that a subject must stand for sampling. In a field environment, markers such as the shoe sole patterns shown in the figure should be used to position the targeted areas of footwear in a consistent location. The addition of such markers will also ensure distance between targeted footwear surfaces and the air jet nozzles or air knives remains approximately same through sampling of successive subjects.

Figure 2:
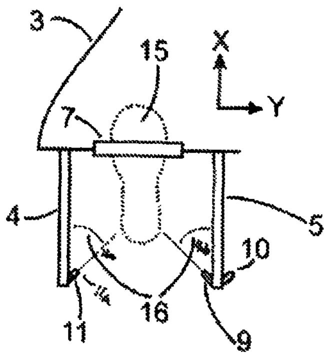
FIG. 2 shows a magnified view of the left air jet nozzle orientation in the X-Y plane.

FIG. 2 shows a magnified view of the area surrounding placement of the left article of footwear with the air jet nozzle orientation in the X-Y plane. Optimal left air jet nozzle 11 orientation is a fixed 45 degrees 16*a* in the X,Y, −Z space, but may be directed through any angle that ensures that air is vectored towards the rear surfaces of the footwear. The left central air jet nozzle is a fixed 45 degrees 16*b* in the X,−Y, −Z space, but may be directed through any angle that ensures that air is vectored towards the rear surfaces of the footwear. The distance from the left air jet nozzle exit 11*a* or left center air jet nozzle exit 9*a* to the footwear surface should optimally be in the range of 5 to 7 inches. The air knife 7 is located centrally above the left side object of footwear targeted. The distance from the exit of the air knife 7*a* to the surface of the footwear should optimally be in the range of 2 to 7 inches.

Figure 3:
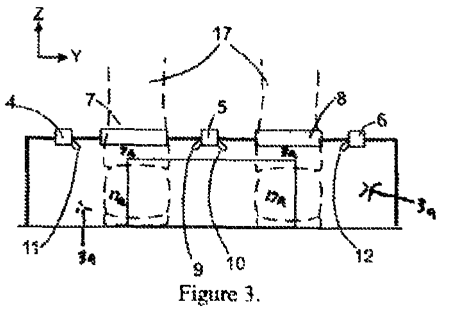
FIG. 3 illustrates the invention from an orientation in the Z-Y plane.

FIG. 3 shows the invention viewed in the Z-Y plane. Outlines of the back of a subject's footwear 17*a* and legs 17 are shown for completion. A left air jet nozzle 11 is directed through X,Y,−Z space, a left central air jet nozzle 9 is directed through the X,−Y, −Z space, a right central air jet nozzle 10 is directed in the X,Y,−Z plane and a right air jet nozzle 12 is directed in the X,−Y,−Z space. The optimal firing sequence of all air jets is from a location 5-7 inches from the target (shoe surface) with distance from the exit of the air knives 7*a*, 8*a*, to the surface of the footwear optimally in the range of 2 to 7 inches. All air jets and air knives release compressed atmospheric gas at 80 psi backpressure, with an air mover flow rate of 620 lps and channel intake 3*a* area of 18.4 square feet; through a release sequence comprising 1) air knives, 2) central jets, then 3) outside jets. With an on-time of 50 ms, off-time of 200 ms, and 200 ms between each release of pressurized gas. Practical limitations in a field deployment environment will likely limit overall sampling time, to between three and five repetitions of the pressurized gas air release sequence. Optimal repetition was determined to be least three times, with a cumulative time of pressurized gas release equaling 6.75 seconds. Particle release efficiency measurements using fluorescent polymer microspheres embedded in sebaceous material have demonstrated the invention as having the ability to consistently remove approximately 20% of known compound from a targeted surface through particle liberation attributed to the four air jets, with each air knife having the ability to liberate a 10% average of known compound from their respective target surfaces.

Figure 4:
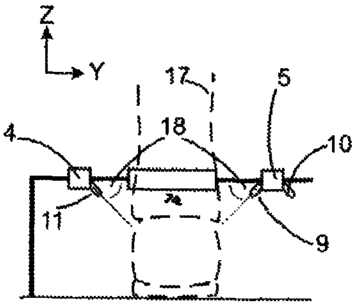
FIG. 4 shows a magnified view of the left air jet nozzle orientation in the Z-Y plane.

FIG. 4 shows a magnified view of the left air jet nozzle orientation on the rear left side of the invention in the Z-Y plane. The optimal left air jet nozzle 11 orientation is 45 degrees within the X, Y,−Z space and the optimal left central air jet nozzle 9 orientation is 45 degrees within the X,−Y,−Z space. The left air jet nozzle 11 may be directed within a range of angles through the X,−Y,−Z and the left central air jet nozzle may be directed within a range of angles through the X,−Y,−Z space to ensure that the airflow from the jet is vectored towards the rear surface of the footwear. Reorientation may become necessary due to an abnormal variance in the foot or footwear size of the target.

Figure 5:
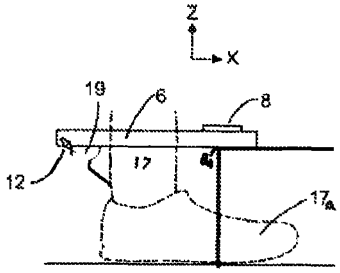
FIG. 5 shows the orientation of the far right air jet nozzle and air knife, above the tongue of footwear in the Z-Y plane.

FIG. 5 shows a right side-view of the invention in the Z-X plane. Outlines of the side of a subject's shoe 17*a* and leg 17 are shown for completion. The optimal right air jet nozzle 12 orientation is 45 degrees in the X,−Y,−Z space 19, but may be directed in any angle that ensures that air flow is vectored towards the rear surface of the footwear. The placement of the right air knife 8 above the tongue of the footwear is shown whereby the right air knife 8 is adjacent to the intake portion of the channel 3*a*.

In an embodiment, the apparatus further includes a detector that is configured to generate a signal responsive to the footwear being position so the airflow is optimized relative to the mouth and gas delivery vehicles.

What is claimed is:

1. An apparatus for collection of particulate matter from footwear, comprising:

a contoured channel suitable for receiving airflow passed over target footwear and conveying such airflow to a sample accumulation feature;

a pressurized gas source to provide gas that is pressurized to gas delivery vehicles that are positioned about a location where the footwear is to be placed and oriented so high velocity airflow from the vehicles impacts target footwear during operation to dislodge particulate matter embedded in or on the target footwear;

an air moving device that draws airflow that passed by the target footwear into the contoured channel so airflow into the contoured channel is maintained at or above 400 liters per second at ambient temperature during procurement of sample by the sample accumulation feature that collects entrained particles liberated from the target footwear, the contoured channel and gas delivery vehicles being configured to maintain consistent particle release from the target footwear and minimize particle spillage from the contoured channel;

where the channel and the gas delivery vehicles are configured to permit reorientation to sample footwear having an a atypical dimension.

* * * * *